US008784458B1

(12) United States Patent
White et al.

(10) Patent No.: US 8,784,458 B1
(45) Date of Patent: Jul. 22, 2014

(54) POLYAXIAL INSERT FOR SURGICAL SCREWS

(75) Inventors: Patrick M. White, West Chester, PA (US); Fabrice Chenaux, Exton, PA (US); Jean-Sebastien Merette, Paoli, PA (US)

(73) Assignee: Greatbatch Medical S.A., Orvin (CH)

( * ) Notice: Subject to any disclaimer, the term of this patent is extended or adjusted under 35 U.S.C. 154(b) by 812 days.

(21) Appl. No.: 12/587,758

(22) Filed: Oct. 13, 2009

Related U.S. Application Data

(60) Provisional application No. 61/104,381, filed on Oct. 10, 2008.

(51) Int. Cl.
*A61B 17/80* (2006.01)

(52) U.S. Cl.
USPC ............ 606/288; 606/290; 606/291; 606/295

(58) Field of Classification Search
USPC ...................... 606/70–71, 280–299
See application file for complete search history.

(56) References Cited

U.S. PATENT DOCUMENTS

| | | | |
|---|---|---|---|
| 4,493,317 A | 1/1985 | Klaue | |
| 5,234,431 A | 8/1993 | Keller | |
| 5,486,176 A | 1/1996 | Hildebrand et al. | |
| 5,976,141 A | 11/1999 | Haag et al. | |
| 6,280,445 B1* | 8/2001 | Morrison et al. | 606/292 |
| 6,322,562 B1 | 11/2001 | Wolter | |
| 6,663,632 B1 | 12/2003 | Frigg | |
| 6,695,846 B2 | 2/2004 | Richelsoph et al. | |
| 6,702,817 B2 | 3/2004 | Beger et al. | |
| 6,890,334 B2 | 5/2005 | Brace et al. | |
| 6,945,975 B2 | 9/2005 | Dalton | |
| 6,955,677 B2 | 10/2005 | Dahners | |
| 7,172,600 B2 | 2/2007 | Beger et al. | |
| 7,537,596 B2 | 5/2009 | Jensen | |
| 2001/0037112 A1 | 11/2001 | Brace et al. | |
| 2003/0078583 A1 | 4/2003 | Biedermann et al. | |
| 2003/0187440 A1 | 10/2003 | Richelsoph et al. | |
| 2003/0187442 A1 | 10/2003 | Richelsoph et al. | |
| 2003/0199876 A1 | 10/2003 | Brace et al. | |
| 2004/0097935 A1 | 5/2004 | Richelsoph et al. | |
| 2004/0167521 A1* | 8/2004 | De Windt | 606/69 |
| 2004/0210219 A1* | 10/2004 | Bray | 606/69 |
| 2005/0165400 A1 | 7/2005 | Fernandez | |
| 2005/0187551 A1* | 8/2005 | Orbay et al. | 606/69 |
| 2005/0234452 A1* | 10/2005 | Malandain | 606/61 |
| 2005/0261688 A1 | 11/2005 | Grady, Jr. et al. | |
| 2006/0276793 A1 | 12/2006 | Berry | |
| 2007/0010817 A1 | 1/2007 | de Coninck | |

(Continued)

FOREIGN PATENT DOCUMENTS

| | | |
|---|---|---|
| DE | 4438264 | 3/1996 |
| DE | 19936061 | 3/2000 |
| DE | 19858889 | 6/2000 |

*Primary Examiner* — Matthew Lawson
(74) *Attorney, Agent, or Firm* — Michael F. Scalise

(57) ABSTRACT

An improved insert for assembly with a bone plate is described. The insert has a first opening adapted to receive a set screw and a second opening adapted to receive a bone screw. The insert is connectable to the bone plate using a set screw. The insert in conjunction with the set screw provides an improved range of relative motion for placing the bone screw at outboard locations with respect to the bone plate. That way, bone fragments that are not necessarily reachable using the bone plate without the insert can be secured together for improved healing.

23 Claims, 11 Drawing Sheets

(56) References Cited

U.S. PATENT DOCUMENTS

| | | |
|---|---|---|
| 2007/0016205 A1 | 1/2007 | Beutter et al. |
| 2007/0055251 A1 | 3/2007 | Huebner et al. |
| 2007/0088360 A1 | 4/2007 | Orbay et al. |
| 2007/0123879 A1 | 5/2007 | Songer et al. |
| 2007/0123884 A1 | 5/2007 | Abdou |
| 2008/0021477 A1 | 1/2008 | Strnad et al. |
| 2008/0114359 A1 | 5/2008 | Murner et al. |
| 2008/0114361 A1 | 5/2008 | Butler et al. |
| 2008/0132900 A1 | 6/2008 | Prien et al. |
| 2008/0140130 A1 | 6/2008 | Chan et al. |

\* cited by examiner

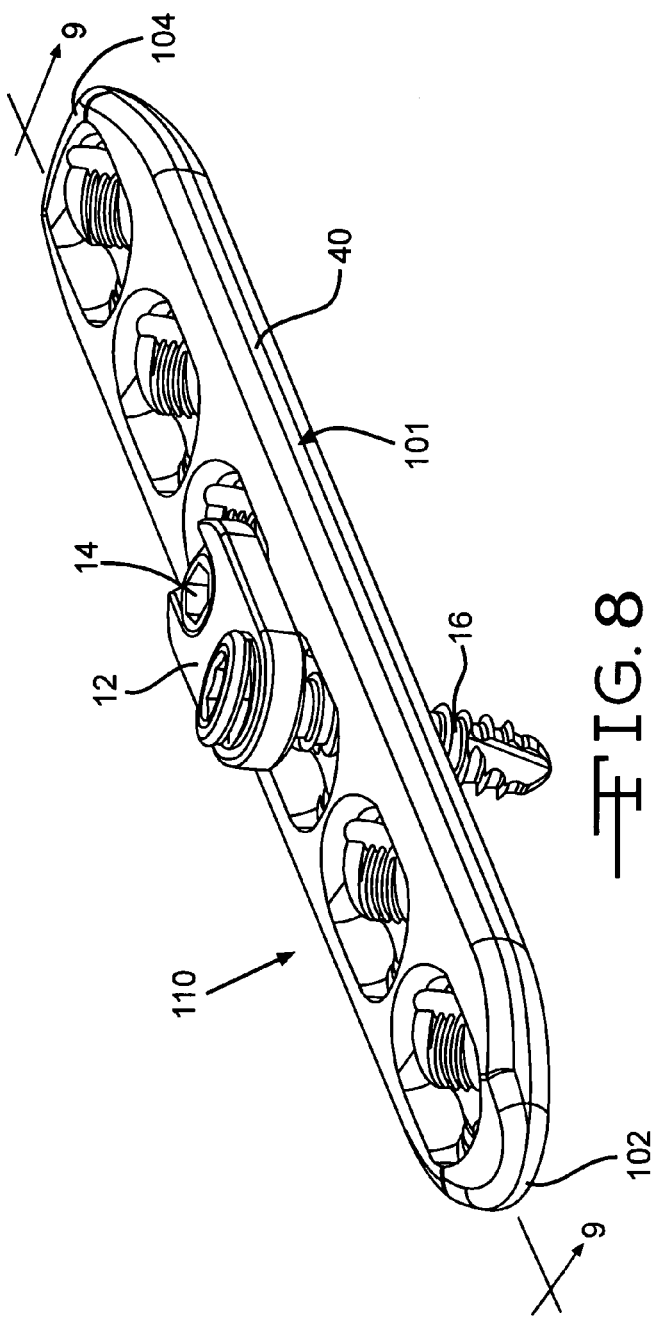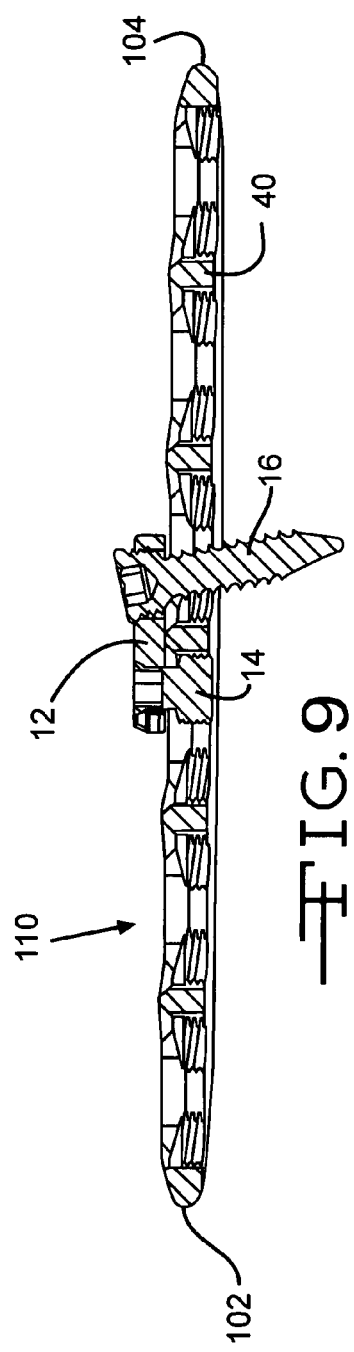

POLYAXIAL INSERT FOR SURGICAL SCREWS

CROSS-REFERENCE TO RELATED APPLICATION

The present application claims priority from U.S. Provisional Application. Ser. No. 61/104,381, filed Oct. 10, 2008.

BACKGROUND OF THE INVENTION

1. Field of the Invention

The present invention is related generally to implantable orthopaedic implants. More specifically, the present invention is related to implantable orthopaedic bone plate inserts.

2. Background Art

Orthopaedic bone plates play a critical role in the healing process of broken bones. Once a bone has been fragmented, it is ideal for the broken bone fragments to be joined back together under compression to promote improved healing. The bone plate is a critical device that is used as a stabilizing bar that bridges the gap in bringing the bone fragments together.

During surgery, a bone plate is inserted next to the fragmented bone of a patient. Compression screws are first placed through the bone plate. They are then anchored into each of the bone fragments and tightened, pulling the bone fragments together under a compression load. Once the compression screws are set in place, locking bone screws are inserted through the bone plate and anchored into the fragmented bone. The locking bone screws in conjunction with the bone plate secure the bone fragments together and ensure that they do not move. However, high tensile stresses are created when the bone fragments are fixated with the locking screws. These tensile stresses could damage the fragile bone fragments and impair the healing process.

The bone plate creates a bridge between bone fragments bearing the tensile load and preventing any movement of the bone fragments. Compression of the bone fragments and complete fixation of the fragments are key elements in promoting improved faster healing of the bone fragments. Bone plates, therefore, are a key element in the bone healing process.

Bone fragmentation, however, is unpredictable. As a result of a traumatic experience, a bone may fragment in multiple erratic locations and present itself in random orientations. Every patient's bones are unique; no two bones will fragment in the same manner in the same orientation. Nevertheless, traditional bone plate technology makes it difficult for a bone plate to be oriented to be utilized correctly for every trauma situation. Bone plates are rigid braces, typically composed of metal, which have historically been designed with fixed threaded holes through which the locking bone screws may not properly align with the matching bone fragment.

It is because of this that additional flexibility is needed to be incorporated into bone plates to afford them increased capability in aligning the locking screw with the matching bone fragments. The present invention is an insert that works in conjunction with an orthopaedic bone plate to increase the number of possible orientations of the locking screw so as to improve the ability of the bone plate to align with bone fragments that are presented in variable orientations with improved bone fragment fixation.

Early bone plate technology comprised bone plates with preexisting threaded holes in combination with threaded locking screws. These earlier bone plate and locking screw combinations secured bone fragments together, however, they lacked the ability to secure bone fragments that were not aligned substantially perpendicular to the threaded locking screw holes of the bone plate.

The preexisting threaded holes of the earlier bone plate technology confined the angle through which the locking screw could be advanced into a bone fragment. For example, with the earlier bone plate and locking screw technology, the physician could only advance the locking screw in the direction of the threaded grooves of the bone plate. The locking screw could only be advanced along the pre-defined perpendicular axis from the bone plate. This limitation created a problem for the physician in that only bone fragments that presented themselves 90° perpendicular from the surface of the bone plate could be secured. Examples of these earlier bone plate and locking screw devices are disclosed in U.S. Pat. No. 5,709,686 to Talus et al.; U.S. Pat. No. 6,206,881 to Frigg et al.; and U.S. Pat. No. 6,306,140 to Siddiqui, the disclosures of which are incorporated herein by reference.

In an effort to increase the degree of freedom in healing fractured bones, plates were developed with locking screws that are able to be inserted at different angles through the bone plate. One such improvement was the development of a bone plate with a tappable contact region as disclosed in U.S. Pat. No. 6,955,677 by Dahners. The disclosure of this patent is incorporated herein by reference. The '677 patent discloses a bone screw with a threaded head that is intended to penetrate into the hole of the bone plate in a tapping fashion. Therefore, the bone screw could be inserted through the bone plate at an angle other than 90° perpendicular from the center of the bone plate cavity. A drawback to this invention, however, is that it utilizes a softer bone plate material which lacks rigidity and stiffness to bear high tensile loads. In addition, over time the softer material of the bone plate could yield to the tensile stresses, resulting in possible movement of the bone fragments that would be detrimental to the proper healing of the bone fragments.

Further, polyaxial screw plate systems have been developed such as those disclosed in U.S. patent application publication 2008/0140130 to Chan et al. as well as U.S. Pat. No. 5,976,141 to Haag et al. The disclosures of these publications are incorporated herein by reference. In the 2008/0140130 application, Chan et al. disclose a threaded head bone screw and drill guide to be used to drill angled holes through the bone plate during surgery. The '141 patent to Haag et al. discloses a bone plate insert that is "snapped" into the bone plate. The insert has an inclined hole that allows the locking or bone screw to be positioned at an angle other than 90° with respect to a plane of the upper or lower surface of the bone plate. These "snap" in inserts are not anchored in place and are prone to slight movements which result in undesirable movement of the bone fragment.

Other previous bone plates rely on a friction fit of the locking screw head to the bone plate to create the connection between insert and bone plate. These frictional fit inserts are predisposed to undesirable movement of the locking screw and, consequently, movement of the bone fragment.

Still other examples of previous bone plate technology are bone plates with a "mushroomed" end providing an enlarged flattened area through which there is an array of pre-defined threaded holes. These types of bone plates are designed to further increase the alignment capability of the locking screw relative to misaligned bone fragments. However, these bone plates, like those previously mentioned, are limited in that they have pre-defined threaded holes or apertures which may not align correctly to the bone fragments after a traumatic experience.

In that respect, the previously described orthopaedic technologies lack the ability to freely rotate about a pivotal axis in securing bone fragments that are off axis from the longitudinal axis plane of the bone plate. In other words, all previously described orthopaedic technologies require that the locking screw pass through the bone plate itself, thereby constraining the locking screw to the limitations of the bone plate.

Accordingly, an orthopedic device is needed that expands the possible locking screw orientations in multiple planes. The present invention is not limited by the geometry of the bone plate in aligning the locking screw to a bone fragment. In addition, the present invention increases the range of angles through which the locking screw can be advanced to a bone fragment. The combination of these inventive features creates multidimensional orientation possibilities of the bone plate.

SUMMARY OF THE INVENTION

The current invention is a bone plate insert with an improved fixation mechanism that extends the reach of the locking or bone screw to bone fragments that don't necessarily reside underneath the bone plate.

The invention consists of an insert that fits into the aperture of a bone plate. The insert has two opposing apertures that provide space for insertion of a set screw and an adjacent locking screw. The set screw secures the insert to the bone plate by tightening the set screw threads into the receiving threads of the bone plate aperture.

Further, the set screw creates a pivotal axis for the bone plate insert. With the use of a set screw, the bone plate insert can now be rotated 360° about the pivotal axis of the set screw, thus increasing the rotation angle of the locking screw into a bone fragment.

As previously mentioned, the invention further includes a locking bone screw that is placed through the insert's second aperture. The present invention does not require that the locking screw pass through the bone plate. The locking screw is first inserted through the bone plate insert and then directly anchored into the bone fragment, or the locking screw is first inserted through both the bone plate insert and then the bone plate before being anchored into the bone fragment.

The present invention also includes a self tapping locking screw with a threaded head that allows the screw to proceed through the insert over a wide range of angles. The threaded head of the locking screw enables the screw to be secured into the material of the insert at different angles other than perpendicular to the plane of the bone plate

BRIEF DESCRIPTION OF THE DRAWINGS

FIG. 8 is a perspective view of the bone plate insert device 10 of the present invention in an alternative orientation in a bone plate 40.

FIG. 9 is a cross-sectional view taken along line 9-9 of FIG. 8 and rotated 180°.

DETAILED DESCRIPTION OF THE PREFERRED EMBODIMENTS

Figure 1:
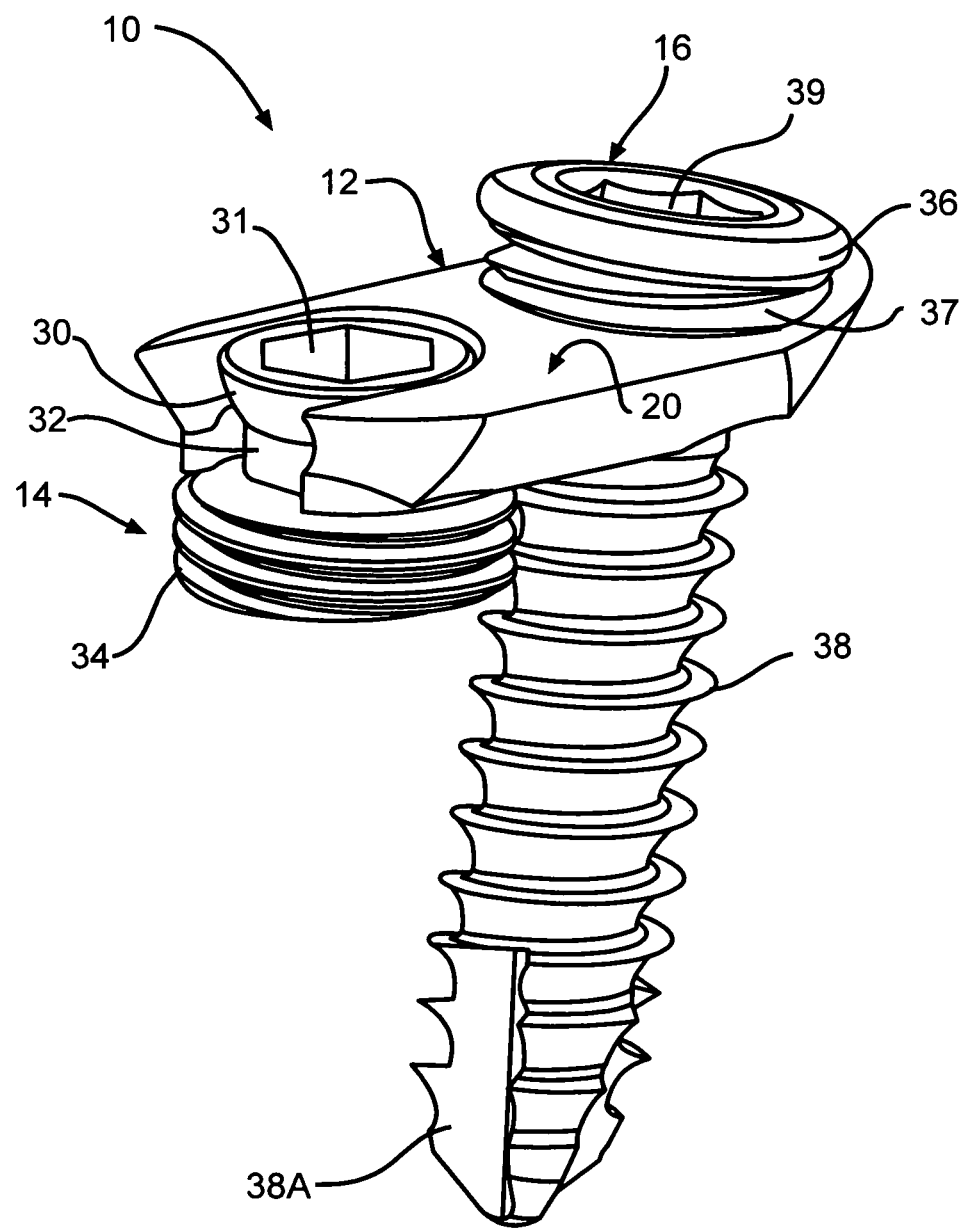
FIG. 1 is a perspective view of an orthopedic bone plate insert device 10 of the present invention.

FIG. 1 is a perspective view of an orthopedic bone plate insert device 10 according to the present invention. The insert device 10 comprises a bone plate insert 12, a set screw 14 and a locking screw 16.

Figure 5:
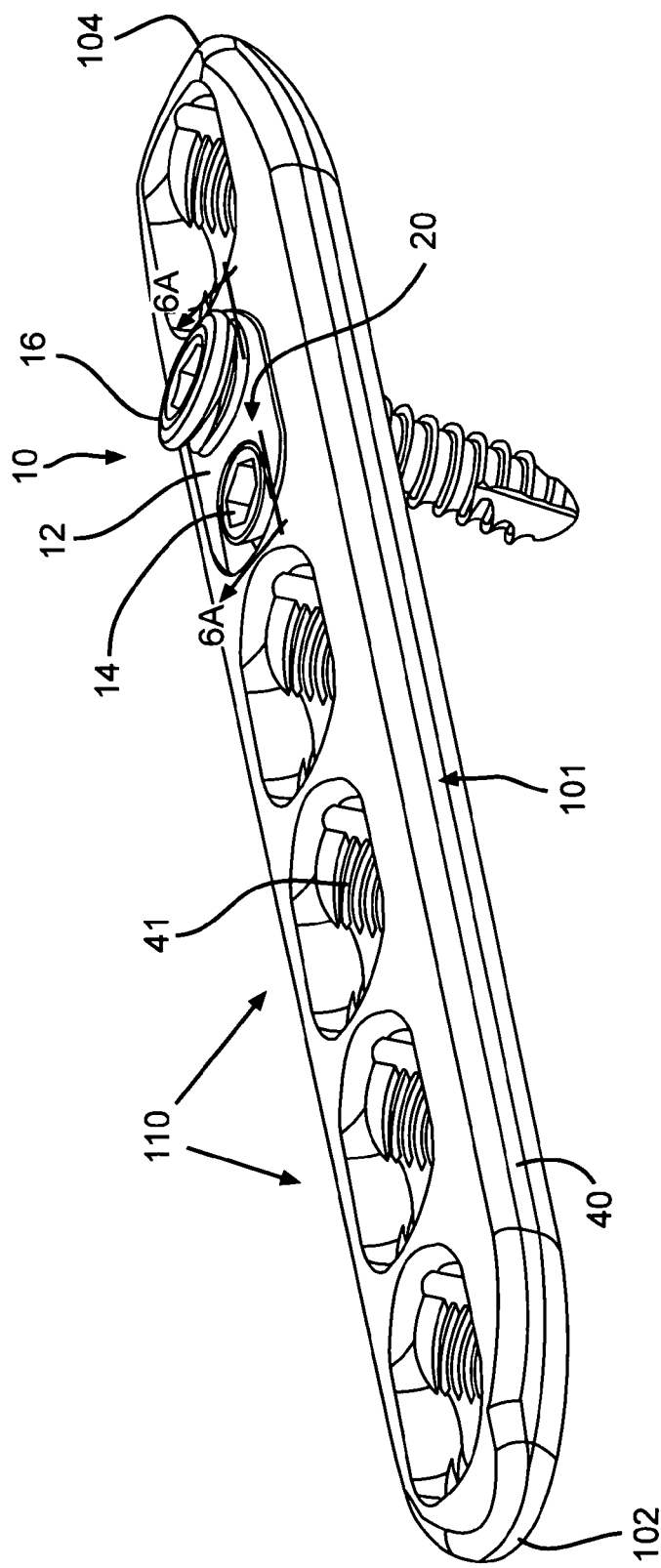
FIG. 5 is a perspective view of the bone plate insert device 10 of the present invention in a preferred orientation in a bone plate 40.

The insert 12 is intended to fit tightly into the complex aperture 110 of a bone plate 40 as shown in FIG. 5. The bone plate 40 comprises a longitudinal axis, a bone-contacting bottom side and a top side with at least one complex apertures extending through the plate thickness from the top to bottom side thereof. The complex aperture 110 is comprised of at least one set of two immediately adjacent holes 112. Each hole 112 has a threaded surface formed therein adapted to lock with threads of a corresponding bone screw. Any two immediately adjacent holes of the complex aperture 110 comprise a compression ramp 116 extending from an oval shaped opening at the top side 106 of the plate downwardly and inwardly part way through the plate thickness to a lower portion having an hourglass shape extending from where the compression ramp ends at the hourglass shape to the bottom side 108 of the bone plate. Threaded surfaces of the immediately adjacent holes 112 meet at an unthreaded intermediate portion 114 forming the hourglass shape. The threaded lower portion of each hole 112 is adapted to lock with threads of corresponding bone screw received therein with the unthreaded intermediate portion 114 there between.

Figure 2:
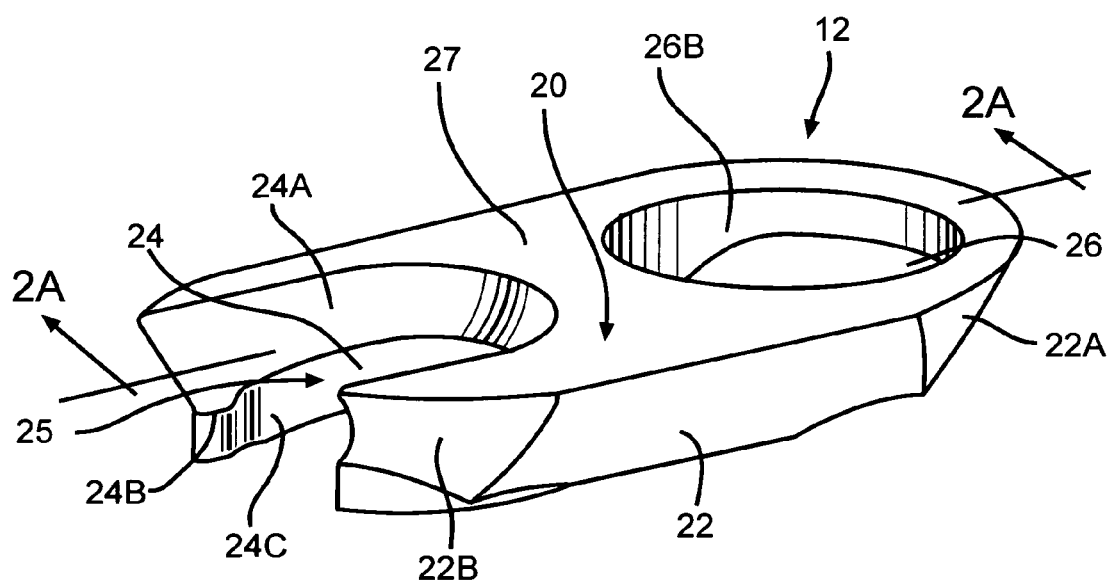
FIG. 2 is an enlarged view of the orthopedic insert 12 shown in FIG. 1.
Figure 2A:
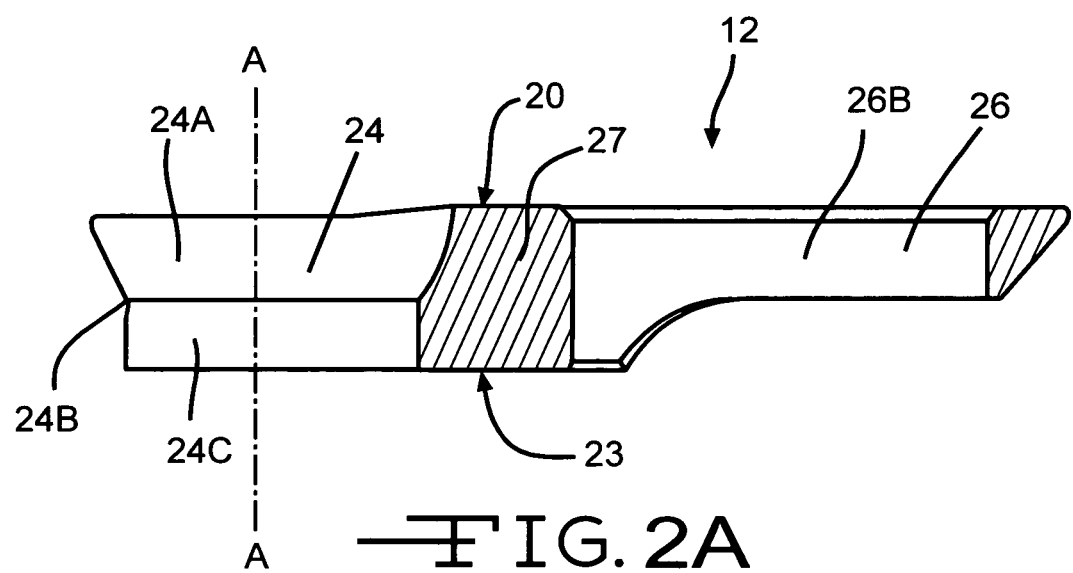
FIG. 2A is an enlarged cross-sectional view taken along line 2A-2A of the orthopedic insert shown in FIG. 2.

As shown in FIG. 2, the insert 12 is a plate-shaped or disc-shaped member having two apertures 24 and 26 separated from each other by a web 27. In this embodiment, apertures 24, 26 are unthreaded and not connected or in communication with each other. The term "disc" is defined in the present invention herein as a flat plate with a pivotal axis A-A (FIG. 2A). The shape of the disc in this embodiment of the present invention is oblong. However, the disc could also have a number of shapes not limited to circular, rectangular, square, and triangular, etc.

The first aperture 24 of the disc 12 receives a set screw (FIG. 1) and in the adjacent second aperture 26, a locking screw 16 is placed. The set screw 14 secures the insert 12 to the complex aperture 110 of the bone plate 40 as shown in FIG. 5.

Figure 3A:
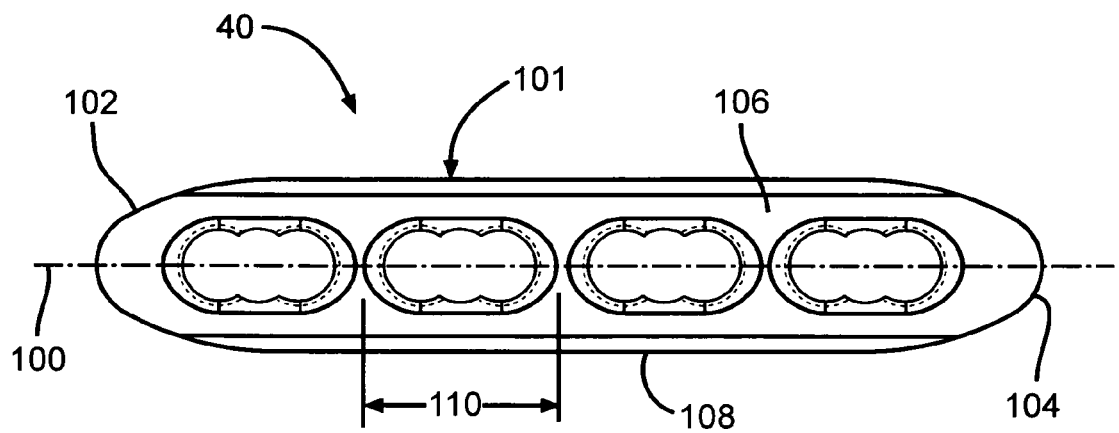
FIG. 3A is a perspective view of an orthopedic bone plate 40.
Figure 3B:
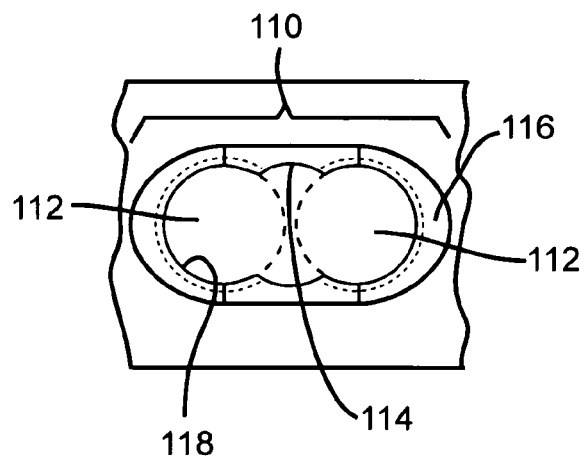
FIG. 3B is an enlarged view of the complex aperture 110 of an orthopedic bone plate 40.

As shown in FIGS. 3A and 3B, the bone plate 40 has a main longitudinal axis 100 that extends between a left end 102 and right end 104, a top surface 106, a bone-contacting bottom surface 108 and a sidewall 101 that surrounds the bone plate 40 and defines a perimeter. A series of complex apertures 110 serve as a space for the placement of the insert 12. Each of the complex apertures consist of adjoining threaded holes 112 that are separated by a bend relief zone 114. The bend relief zone 114 relieves stress created by insertion of the insert 12 and screws in the complex aperture 110.

The complex aperture 110 is further defined by a compression ramp 116 that slopes downwardly and inwardly from the top surface 106 of the bone plate 40 towards the threaded apertures 112. The apertures 112 are defined by respective radiused threaded wall surfaces 118. That way, the compression ramp 116 creates a nest for the insert 12 directly above the threaded apertures 112. Further disclosure about the bone plate 40 can be obtained through U.S. patent application Ser. No. 12/307,128, which is incorporated by reference herein.

The set screw 14 (FIG. 4A) is dimensioned and sized in a manner such that its threads 34 align with the threads 41 of the bone plate cavity 110. The set screw 14 anchors the insert 12 to the bone plate 40.

The locking screw 16 (FIG. 4B) is placed through the second aperture 26 of the insert 12. The locking screw threads 38 have self tapping double lead threads with a preferred thread pitch of about 1 mm. However the thread pitch can vary from about 0.5 mm to about 5 mm. The locking screw threads 38 are designed to be self tapping such that the locking screw 16 can be placed through the unthreaded aperture 26 of insert 12 and or the bone plate 40 at extreme angles other than from 90° relative to the top or bottom surfaces 106, 108 of the plate. The self tapping nature of the locking screw threads 38 also allow the locking screw 16 to easily drill into a bone fragment. As in FIG. 1, a further embodiment of the locking screw 16 also includes tapping flutes 38A.

Figure 10:
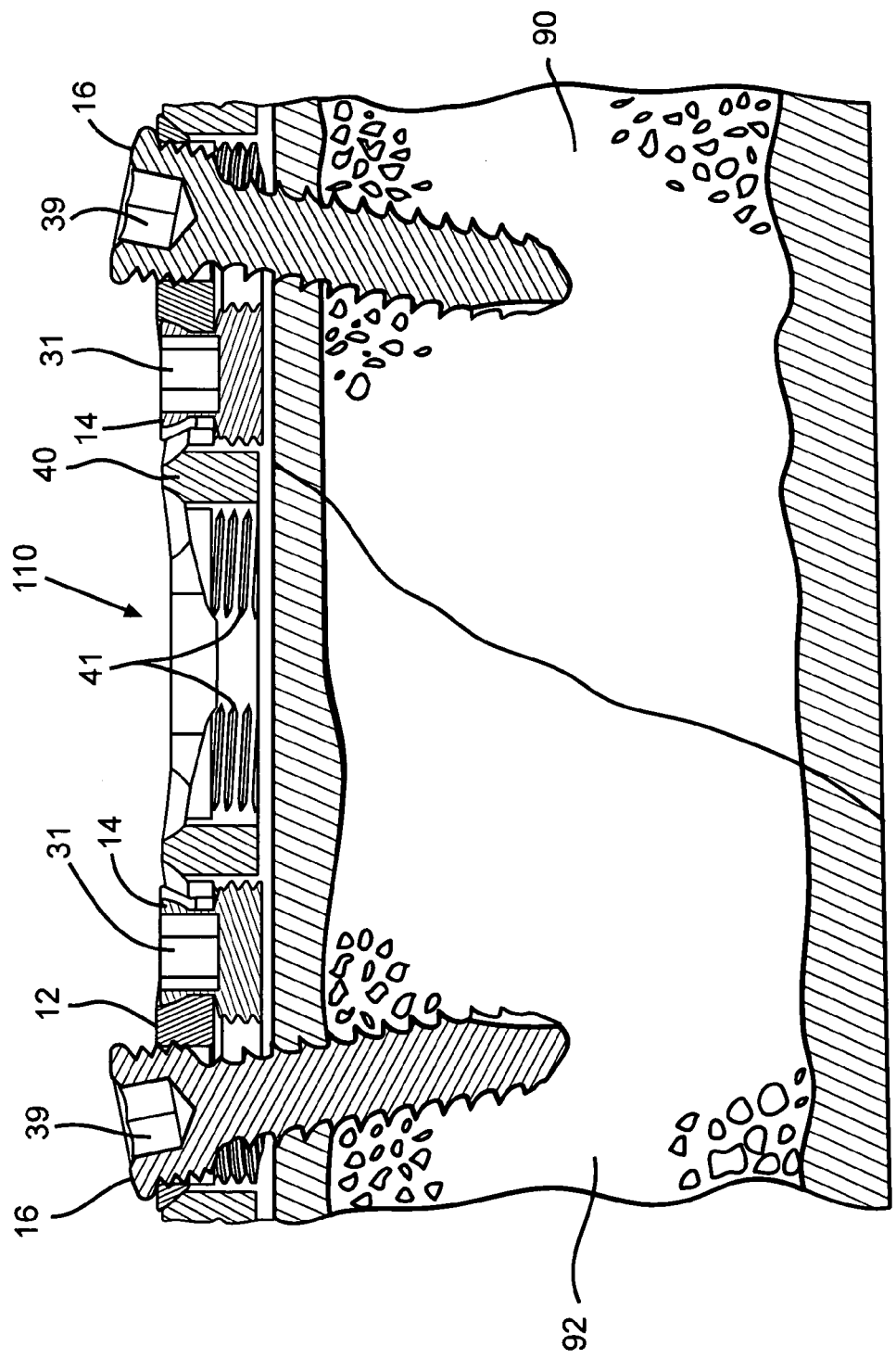
FIG. 10 is a cross-sectional view of the bone plate insert device 10 of the present invention being used with a bone plate 40 to secure two bone fragments 90 and 92 together.

As shown in FIG. 10, the locking screw 16 is designed to anchor into a bone fragment and secure it to the bone plate therefore stabilizing the bone fragment 90, 92 from moving.

Although it is preferred that the apertures 24 and 26 of the insert 12 are unthreaded, one could design the insert 12 with threaded or grooved apertures 24 and 26 that accept the receiving threads or grooves of a screw. Furthermore, either or both of the apertures 24 and 26 of the insert 12 can be threaded or grooved to accept a screw.

FIG. 2 shows a perspective view of the bone plate insert 12 and FIG. 2A shows a cross-sectional view of the insert 12. The insert 12 has a top surface 20, a front surface 22, a back surface (not shown) and a bottom surface 23. The top surface 20 is planar and parallel to the bottom surface 23. The insert 12 has a perimeter that is defined as a boundary around the entire length and width of the insert 12.

Both the front surface 22 and back surface (not shown) are contoured to fit into the complex aperture 110 of the bone plate 40. The front surface 22 and corresponding back surface are angled downwardly and inwardly from the top surface 20 to the bottom surface 23 in such a way that the width of the top surface 20 is wider than the width of the bottom surface 23. The insert 12 has a left front segment 22A and a right front segment 22B. Both segments 22A and 22B have a curved and tapered surface. The curved surface of segments 22A and 22B are designed to correspond to the curved left and right inner cavity surfaces of the bone plate 40. Although not shown in FIG. 2, there are corresponding left and right segments similar in shape, size and appearance to that of the left front segment 22A and the right front surface segment 22B on the back side of the insert 12.

The curved surfaces 22, 22A and 22B of the insert 12 are designed to be in communication with the contoured complex aperture 110 of the bone plate 40 (FIGS. 3A, 3B). The complex aperture 110 creates a compression ramp such that the contours of the insert 12 fit securely therein, thus providing a snug fit that prevents movement of the insert 12 and attached locking screw 16. Should such movement occur, undesirable movement of the bone fragments 90, 92 could result.

The bone plate insert 12 has a preferred length ranging from about 10 mm to about 50 mm, a width ranging from about 5 mm to about 20 mm and a depth ranging from about 0.5 mm to about 5 mm. Although not preferred, the length of the bone plate insert 12 may extend from about 50 mm to about 500 mm. The added length of the insert extends the reach of the locking screw, particularly when the longitudinal axis of the insert is perpendicular to the longitudinal axis of the bone plate.

It is preferred that the bone plate insert 12 be made from commercially pure grade 3 titanium. However, other biocompatible metals and polymers such as stainless steel and polyetheretherketone (PEEK) can also be used. It is preferred that the bone plate insert 12 be made from a material that is relatively softer, less stiff or of a lower durometer than that of the bone plate 40. It is also preferred that the set screw 14 and the locking screw 16 be made from a material that is relatively harder, stiffer or of a higher durometer than that of the insert 12.

Constructing the bone plate insert 12 from a relatively softer material than that of the bone plate 40 enables the locking screw 16 to more easily tap or bore into the insert 12 without sacrificing the strength, rigidity and tensile load bearing properties of the bone plate 40. A bone plate insert 12 made of a relatively softer material in conjunction with a locking screw made of a relatively harder material allows for easier alignment of the locking screw to the bone fragment 90, 92. That's because the locking screw 16 is not confined to a pre-existing threaded aperture.

In addition, designing the locking screw 16 and set screw 14 from a material that is relatively harder than the insert 12 ensures that the insert 12 will yield and deform around the advancing screw 12 or 16. This is particularly beneficial if the advancing screw 12 or 16 is proceeding in a direction that is not aligned with the longitudinal axis of the respective apertures 24, 26 of the insert 12. That's because the relatively softer material of the insert 12 deforms around the threads of the advancing screw, thereby securing the screw in place.

Although it is preferred that the insert 12 be made of a material that is relatively softer than that of the bone plate 40, or of the set and locking screws 14 and 16, one could design the insert 12 from a material of the same hardness or from a material that is relatively harder. For example, if the insert is designed with threaded apertures, as mentioned before in a previous alternate embodiment, it would be beneficial for the insert 12 and the set and locking screws 14 and 16 to be made from a material with a similar hardness, such as (Ti-6Al-4V). This ensures the long term rigidity of the insert 12 threads.

The insert 12 has two apertures. The first aperture 24, as shown on the left side of the insert 12 in FIG. 2, is formed as an oblong inlet 25. The shape of the oblong inlet 25 of aperture 24 is similar to that of a slot. The left side wall of cavity 24 has been removed to form the inlet design. In other words, the inlet 25 extends through the perimeter of the insert 12 and the thickness of the insert 12. The inlet 25 allows for the set screw 14 to be easily slid into place in the aperture 24 from a lateral direction.

Since the set screw 14 is designed with threads 34 that mate with the threads of the wider diameter bone plate aperture 112, the threaded shaft 34 of the set screw is wider than that of the insert aperture 24. Therefore the set screw 14 is placed into position by sliding the neck 32 of the set screw into the inlet 25 and then into the opening 24 through the perimeter of the insert 12. The set screw head 30 extends upwardly and outwardly from the neck 32 and is designed to be wider than both the inlet 25 and the opening 24. That is to improve ease of tightening and ensure that the set screw 14 does not fall out of the aperture 24. This design is particularly useful in pre-assembly of the set screw 14 with the insert 12.

Aperture 24 is divided into two regions, a top region 24A and a bottom region 24C. The top region 24A has an angled curved surface with a downwardly and inwardly extending slope that corresponds to the curved surface of the head 30 of the set screw 14. The corresponding concave surface of the top region 24A and convex surface of the set screw head 30 allow for the set screw 14 to be easily slid into position in the inlet aperture 24.

The top region 24A of the aperture 24 is convex and slopes downwardly and inwardly until it reaches a protruding ridge 24B at about mid-way through the thickness of the aperture. It is at this midpoint in the aperture where the neck 32 of the set screw 14 is placed. The protruding ridge 24B contacts the head 30 of the set screw 14 and ensures that the set screw 14 does not fall out of the aperture 24. The second, bottom region 24C of aperture 24 has a surface that is aligned 90° perpendicular to the top surface 20 and bottom surface 23 of the insert 12. The bottom region 24C encompasses the surface of the aperture 24 wall extending from the protruding ridge 24B downwardly toward the bottom surface 23 of the insert 12. Both the top region 24A and bottom region 24C are smooth and unthreaded. Aperture 24 has a preferred length ranging from about 5 mm to 20 mm, a width ranging from about 2 mm to about 10 mm and a depth ranging from about 0.5 mm to about 5 mm.

The insert 12 has a second aperture 26 that is adjacent to aperture 24. Aperture 26 is a circular opening with a cylindrical inner wall surface 26B. In a preferred embodiment, a longitudinal axis centered along the cylindrical inner wall surface 26B of aperture 26 is perpendicular to the top surface 20 and bottom surface 23 of the insert 12. Aperture wall surface 26B is smooth and extends through the thickness of the insert 12 from the top surface 20 to the bottom surface 23 thereof. Aperture 26 preferably has a diameter ranging from about 5 mm to about 20 mm and a depth ranging from about 0.5 min to about 5 mm. A web 27 ranging from about 1 mm to about 5 mm separates the apertures 24 and 26 from each other.

Figure 4A:
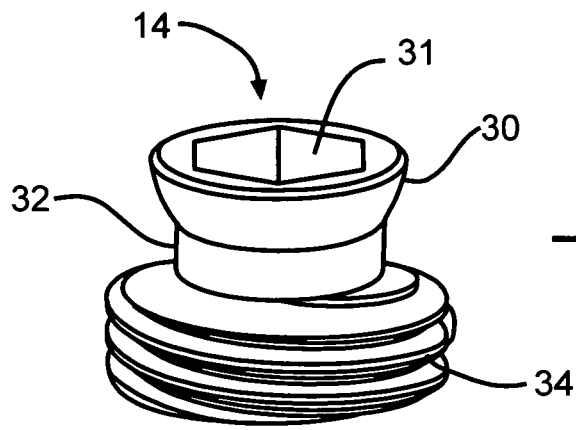
FIG. 4A is an enlarged perspective view of the set screw 14.

As previously mentioned, the orthopedic bone plate insert device 10 comprises a set screw 14 and a locking screw 16 in addition to the insert 12. The set screw 14 is a required integral part of the present invention. The set screw 14 anchors the insert 12 into the bone plate 40. FIG. 4A shows an embodiment of the set screw 14. The set screw head 30 is preferably round with a bowl shape. Preferably, the set screw head 30 has a socket opening 31 at the top of the head 30 in which an Allen wrench can be used to apply torque. However, the opening 31 at the top of the screw head 30 is not limited to just a socket design, but can also be slotted, have a Phillips shape, be in the form of a star, square, triangle or other shape. The diameter of the set screw head 30 is from about 3 mm to about 15 mm and should not be smaller than the width of the bottom region 24C of the cavity 24. The set screw neck 32 is circular and should have a length that is about the same as the length of the bottom region 24C. The set screw threads 34 are designed to secure themselves with an interference fit into the receiving threads 41 of the cavity of the bone plate 40. The set screw threads 34 are double helix with a preferred thread pitch of about 0.45 mm to about 0.60 mm. For example, if the pitch of the threads 41 of the bone plate 40 are 0.50 mm, the pitch of the set screw threads 34 should be 0.55 mm to create the desired interference fit.

The overall length of the set screw 14 is from about 0.5 mm to about 5 mm. It is preferred that the set screw 14 be made out of a biocompatible titanium alloy material such as (Ti-6Al-4V). Other biocompatible metals and polymers include, but are not limited to, stainless steel and PEEK can also be used.

Figure 4B:
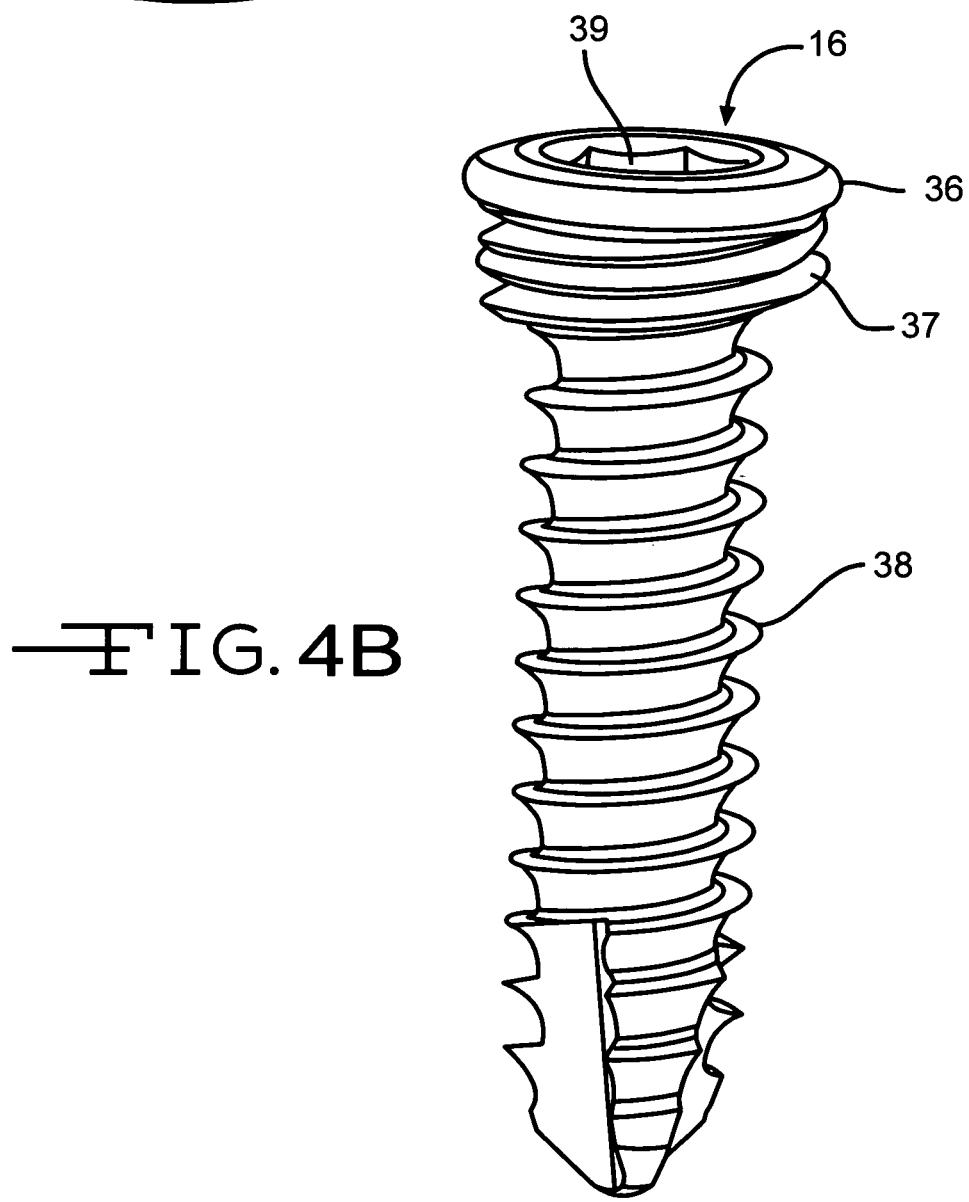
FIG. 4B is an enlarged perspective view of the locking screw 16.

FIG. 4B shows an enlarged view of an embodiment of a locking screw 16. The locking screw 16, also referred to as a bone screw, has a length extending from a head 36 to the distal end of a threaded portion 38. The locking screw head 36, as depicted in FIG. 4B is cylindrical in shape with a tapered thread. The first threaded portion 37 is sized to threadingly mate with the threads (if they exist) in the second aperture 26, or if aperture 26 is unthreaded, to self-tap therein. The second threaded portion 38 is designed to seat in bone material, and the like.

The tapered tip design of the locking screw head 36 is intended to be able to embed itself into the insert 12. The tapered threaded head 36 of the locking screw is designed to dig into the material of the insert 12. This locking screw head 36 design enables the locking screw 16 to be placed at an extreme angle. For example, the screw 16 can thread into the insert 12 at angles other than coaxial to the central longitudinal axis of the cylindrical aperture 26. Preferably the locking screw head 36 has a socket opening 39 at the top of the head in which an Allen wrench can be used to apply torque. However, the opening 39 at the top of the screw head 36 is not limited to just a socket design, but can also be slotted, have a Phillips shape, be in the form of a star, square, triangle or other shape. The diameter of the set screw head 32 is from about 3 mm to about 25 mm.

The overall length of the locking screw 16 is from about 0.5 mm to about 15 cm. The diameter of the threaded portion 38 of the locking screw 16 should be slightly larger than that of the aperture 26. In a preferred embodiment, the diameter of the threaded portion 38 of the locking screw is about 0.5 mm larger in diameter than that of the aperture 26. This size differential creates an interference fit between the locking screw 16 and insert 12 that allows for the locking screw to be inserted at angles other than perpendicular to the planar top or upper surface 20 of the insert 12. The locking screw 16 taps and digs into the material of the insert 12. In a preferred embodiment, the locking screw 16 is made of a biocompatible titanium alloy material such as (Ti-6Al-4V). Other biocompatible metals and polymers including, but not limited to, stainless steel and PEEK can also be used. It is preferred that the locking screw 16 be made of a material that is relatively harder than the insert 12. For example, one could make the locking screw 16 from a hard stainless steel metal and the insert 12 out of a softer PEEK polymer. A softer insert 12 material is preferred because the softer material will more easily deform around the harder material locking screw 16 making it easier for the locking screw 16 to penetrate into the insert 12. In addition, the softer insert 12 material deforms around the locking screw 16, adding an additional means of securing the locking screw into place.

FIG. 5 shows a perspective view of the bone plate insert device 10 in a preferred orientation in a bone plate 40. In this preferred orientation, the insert 12 is placed in one of the complex apertures of the bone plate 40 in such a manner that the upper surface 20 of the insert 12 is substantially co-planar, or only a relatively small distance above, the upper surface of the bone plate 40. More specifically, in the preferred embodiment in FIG. 5, the perimeter of the insert 12 is nested into the cavity formed by the compression ramp 115 of the complex aperture 110 of the bone plate 40. As shown in FIG. 5, the locking screw 16 has been advanced through the insert 12 and the bone plate 40. The locking screw 16 is shown in an orientation that is angled with respect to an orientation perpendicular to the planar upper surface 20 of the insert 12 and bone plate 40. The set screw 14 has been advanced into the insert, securing the insert 12 to the bone plate 40.

Figure 6:
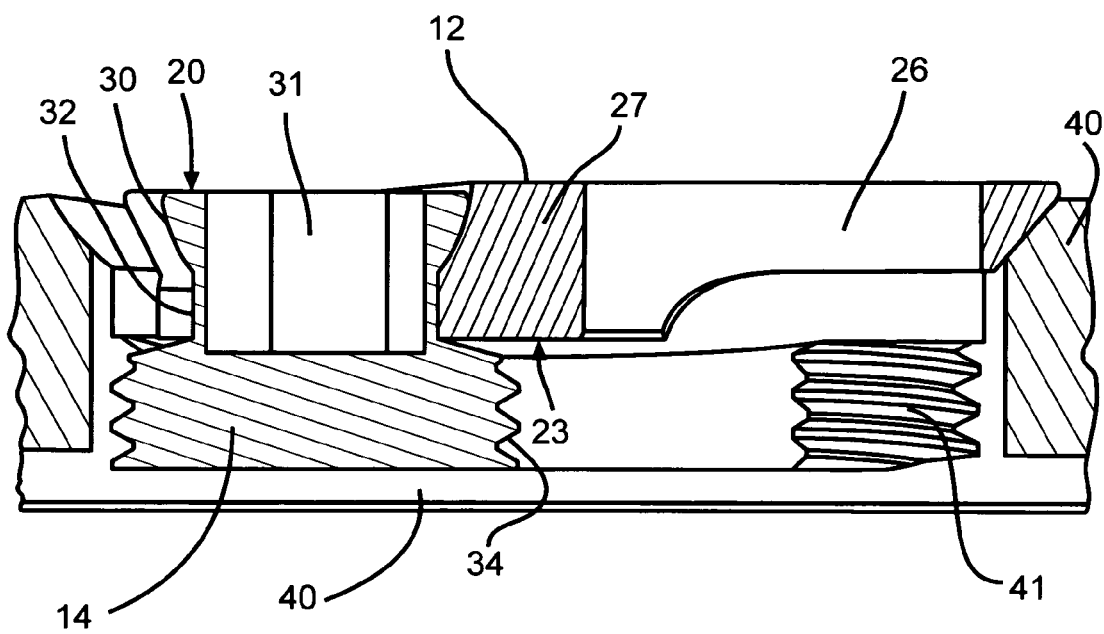
FIG. 6 is an enlarged cross-sectional view of the bone plate insert device 10 shown in FIG. 5, but without the locking screw 16.

FIG. 6 shows an enlarged cross-sectional view of an embodiment of the inert 12 in the complex aperture 110 of a bone plate 40. The set screw 14 is locked and engaged in the threads 41 of the bone plate 40. This perspective view shows the insert 12 engaged in the bone plate 40 without the locking screw 16.

Figure 6A:
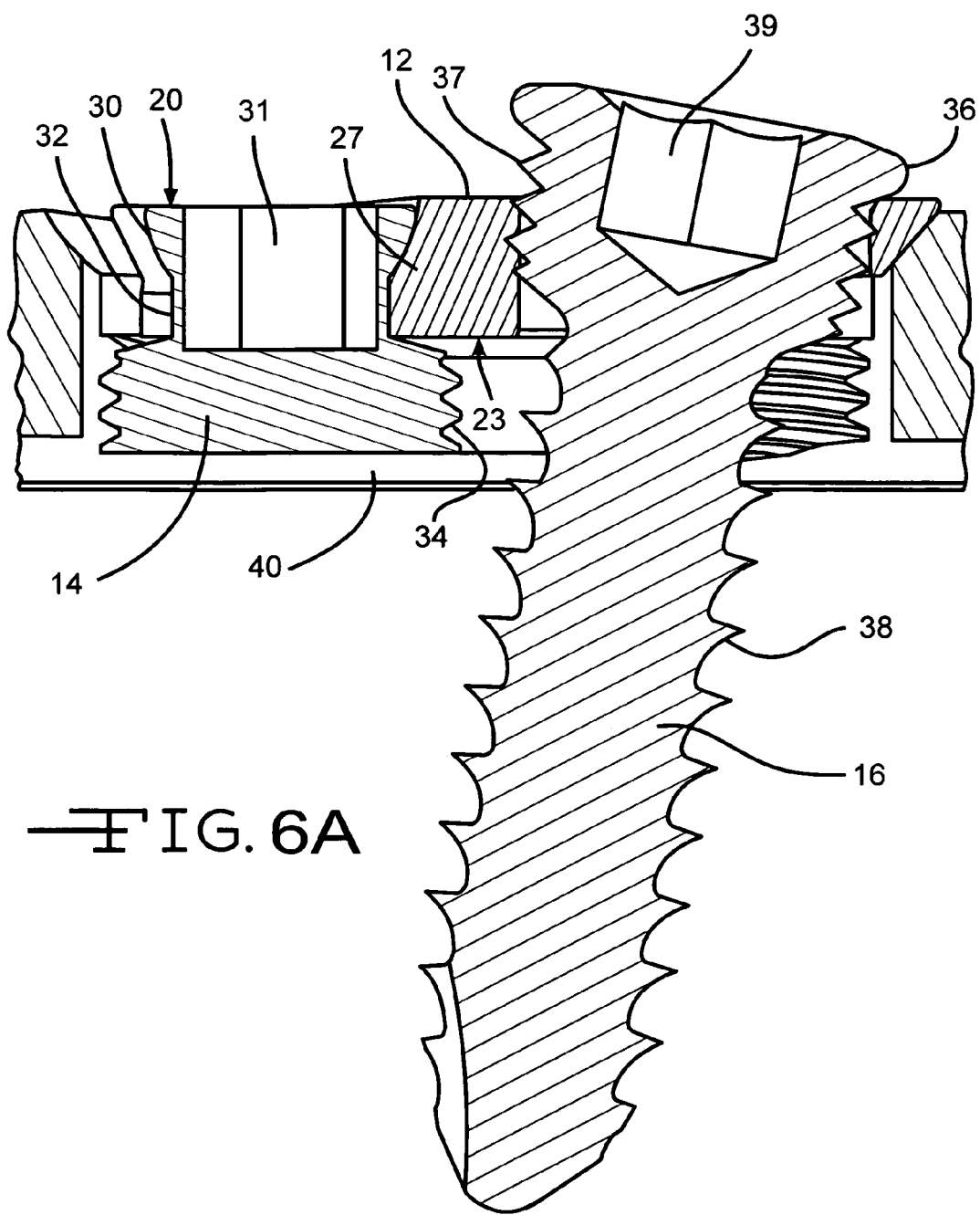
FIG. 6A is an enlarged cross-sectional view taken along line 6A-6A of the bone plate insert device 10 shown in FIG. 5.

FIG. 6A shows an enlarged cross-sectional view of an embodiment of the insert 12 in a complex aperture 110. The set screw 14 is locked and engaged in the bone plate threads 41 and the locking screw 16 is shown after being advanced through the insert 12 and bone plate 40. The first threads 37 of the locking screw 16 are shown secured into the material of the insert 12 near the second insert aperture 26. As the cross sectional view of FIG. 5 shows, the apertures 24 and 26 of the insert 12 are unthreaded. Also shown in FIG. 6 are the first and second threads 37, 38 of the locking screw 16. One can see how the material of the insert 12 deforms around the first threads 37 to secure the locking screw 16 into the insert 12.

One reason for using the insert device 10 of the present invention in conjunction with the bone plate 40 is because of the varied angles of orientation it affords the bone screw 16. For example, the threads 41 of the complex apertures 110 of the bone plate 40 have a fixed angle of orientation with respect to the bone plate bottom surface. A surgeon may desire to orient the bone screw 16 at an angle other than that of the threads 41. With the insert 12 nestled in the complex aperture 110, such flexibility is possible. As previously discussed, the insert 12 is of a relatively softer material than that of the bone plate 40. This provides the bone screw 16 with being able to self tap in the second aperture 26 of the insert. This self-tapping characteristic means that the screw 16 can be advanced into a bone fragment 90, 92 at orientations other than those provided by the threads 41 of the complex aperture 110 of the bone plate 40.

Figure 7:
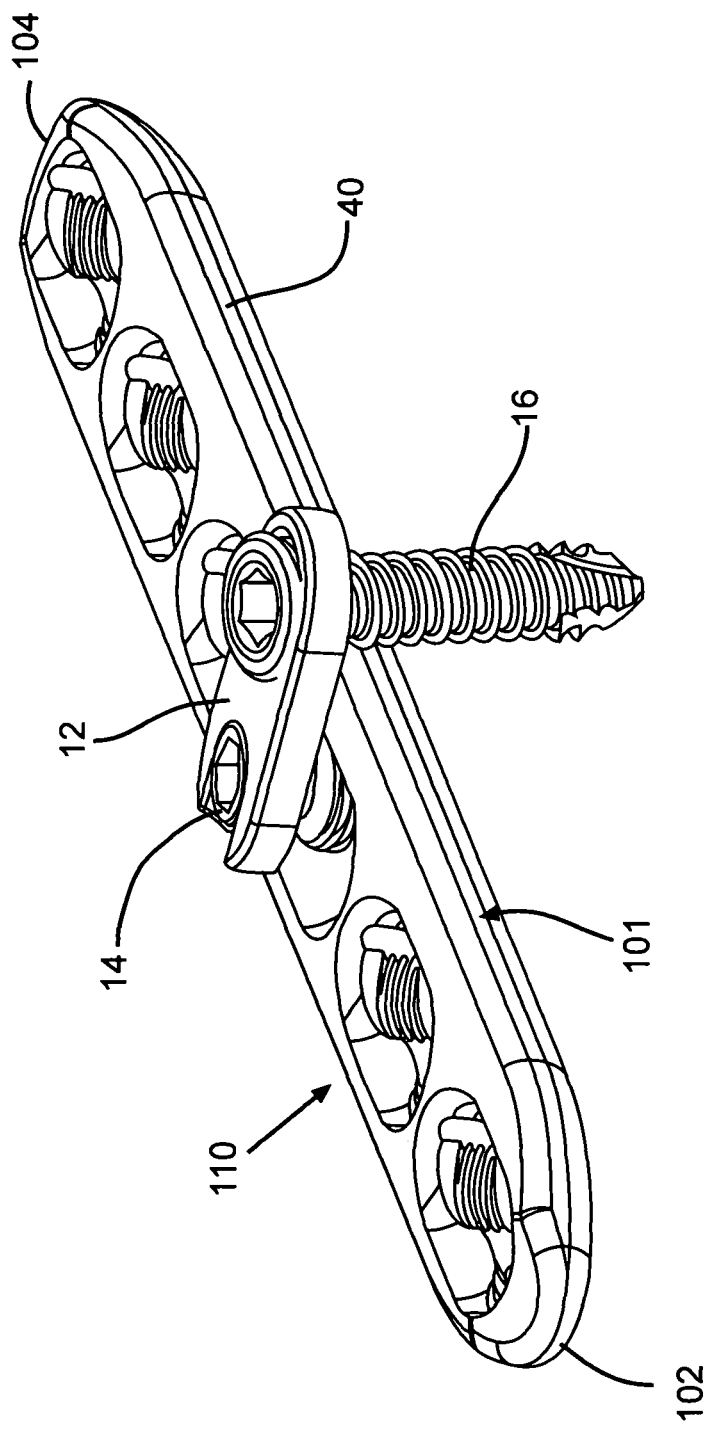
FIG. 7 is a perspective view of the bone plate insert device 10 of the present invention in an alternative orientation in a bone plate 40.

FIG. 7 shows an alternate embodiment of the insert 12 and locking screw 16 in relationship to the bone plate 40. As shown in the figure, the longitudinal axes of the insert 12 and the bone plate 40 are not aligned. Instead, they are angled with respect to each other. As such the locking screw 16 does not pass through the bone plate 40 but is adjacent to and outside of the perimeter of the bone plate 40. FIG. 7 illustrates the pivotal axis that the set screw 14 creates for the insert 12. The combination of a self tapping locking screw 16 that can be inserted at multiple, non-prescribed angles and a pivotal axis of rotation created by the set screw 14 affords the physician tremendous latitude in the number of possible positions in placing the locking screw 16 into a bone fragment 90 and 92 (FIG. 10).

In that respect, the insert 12 can be rotated 360° about the pivotal axis created by the set screw 14. This allows the connected locking screw 16 to be rotated along with the insert 12 without the geometric constraints of the bone plate 40. For example, in a trauma situation in which a bone has been fractured and displaced in multiple locations, it is now possible to secure and stabilize bone fragments that are not in alignment with or necessarily located underneath the bone plate. Therefore, there is a reduction in trauma to the patient during surgery, the operation may take less time and may be less need for implanting multiple bone plates.

In an alternate embodiment, the curved surfaces 22, 22A and 22B of the insert 12 are of the same thickness shown in FIG. 7 of the present invention. As the figure shows, the thickness of the edge of insert 12 is consistent around the perimeter. This is particularly beneficial when the locking screw 16 is outside the perimeter of the bone plate 40 as shown in FIG. 7 because the added thickness around aperture 26 increases the stability and rigidity in supporting the locking screw 16.

FIG. 8 shows another alternate orientation of the present invention. In this depiction, the locking screw 16 is placed through an adjoining complex aperture 110 of the bone plate 40 in respect to the complex aperture 110 in which the set screw 14 resides. This is an example of the extended range of motion that the present invention affords. As one can see, the set screw 14, which anchors the insert 12 in place to the bone plate 40, creates a pivot axis about which the insert 12 with the locking screw 16 can be rotated.

FIG. 9 shows a cross-sectional view of the embodiment shown in FIG. 8. As the figure shows, the set screw 14 is secured in the bone plate 40 in a first complex aperture 110 and the locking screw 16 is placed through the insert 12 and an adjoining complex aperture. As the figure shows, the threads of the set screw 34 are engaged in the threads 41 of the complex aperture 110 of the bone plate 40 and the threads of the locking screw 38 are threaded into the insert 12 and advanced through the second complex aperture of the bone plate 40.

FIG. 10 shows a cross sectional view of the present invention joining two bone fragments 90 and 92 together. As the figure shows, two locking screws 16 have been advanced through two inserts 12 and through two complex apertures 110 of respective bone plates 40. The locking screws 16 are shown threaded in the insert 12 received in the bone plate 40 to penetrate into the bone fragments 90 and 92.

It is appreciated that various modifications to the inventive concepts described herein may be apparent to those of ordinary skill in the art without departing from the spirit and scope of the present invention.

What is claimed is:

1. An insert disc for a bone plate, the insert disc comprising:
   a) an outer sidewall providing an insert disc thickness extending from a bottom surface to a top surface of the insert disc, wherein at least one of the top and bottom surfaces is planar;
   b) a first, unthreaded aperture extending through the insert disc thickness, wherein the first aperture comprises:
      i) a top region sidewall sloping downwardly and inwardly part-way through the insert disc thickness from a first diameter at the top surface to a ridge having a second diameter less than the first diameter, and
      ii) a bottom region sidewall extending from the ridge to the bottom surface, wherein the bottom region sidewall is aligned substantially perpendicular to the at least one of the top and bottom planar surfaces of the insert disc;
   c) a second, threaded aperture extending through the insert disc thickness; and
   d) an inlet that extends through the outer sidewall of the insert disc and is in open communication with the first, unthreaded aperture, but not the second, threaded aperture,
   e) wherein the first and second apertures are not in open communication with each other.

2. The insert disc of claim 1 wherein the second aperture has a circular cross-section aligned along a first longitudinal axis that is perpendicular to at least one of the top and bottom surfaces of the insert disc.

3. The insert disc of claim 1 wherein the top and bottom surfaces are planar and parallel to each other.

4. The insert disc of claim 1 being composed of a biocompatible metal or polymer.

5. The insert disc of claim 1 wherein the inlet is configured for movement of a set screw through the sidewall and subsequently receipt in the first aperture.

6. The insert disc of claim 1 wherein the first and second apertures are aligned along a second longitudinal axis of the insert disc.

7. The insert disc of claim 1 wherein the inlet is oblong.

8. The insert disc of claim 1 wherein the second aperture is enclosed within the perimeter of the insert disc.

9. The insert disc of claim 1 wherein both of the top and bottom surfaces are planar.

10. An assembly comprising an insert disc for threadingly receiving a bone screw threaded into a bone plate, the assembly comprising:
 a) a bone plate comprising:
  i) a plate thickness extending from a bone-contacting bottom side to a top side;
  ii) at least a first plate aperture and a second plate aperture extending through the plate thickness, at least one of the first and second plate apertures having threads;
 b) a bone screw having threads that are adapted to threadingly engage with the threads of the at least one of the first and second apertures of the bone plate;
 c) an insert disc comprising:
  i) an outer sidewall providing an insert disc thickness extending from a bottom surface to a top surface of the insert disc, wherein at least one of the top and bottom surfaces is planar;
  ii) a first, unthreaded aperture extending through the insert disc thickness, wherein the first aperture comprises:
   a top region sidewall sloping downwardly and inwardly part-way through the insert disc thickness from a first diameter at the top surface to a ridge having a second diameter less than the first diameter, and
   a bottom region sidewall extending from the ridge to the bottom surface, wherein the bottom region sidewall is aligned substantially perpendicular to the at least one of the top and bottom planar surfaces of the insert disc;
  iii) a second, threaded insert aperture extending through the insert disc thickness; and
  iv) an inlet that extends through the outer sidewall of the insert disc and is in open communication with the first, unthreaded aperture, but not the second, threaded aperture,
  v) wherein the first and second insert apertures are not in open communication with each other; and
 d) wherein with the insert disc contacting the bone plate, a set screw received in the first, unthreaded insert aperture is threadingly engageable with the threads of the at least one of the first and second plate apertures.

11. The assembly of claim 10 wherein the bone plate comprises at least one complex aperture extending through the plate thickness from the top side to the bottom side thereof, the complex aperture comprising at least one set of immediately adjacent first and second plate apertures having threaded surfaces formed therein adapted to threadingly engage with threads of the bone screw.

12. The assembly of claim 11 wherein the complex aperture comprises an unthreaded compression ramp extending from an opening at the top side of the bone plate downwardly and inwardly part way through the plate thickness to a threaded lower portion adapted to threadingly engage with threads of the bone screw received in either one or both of the immediately adjacent first and second plate apertures.

13. The assembly of claim 11 wherein the immediately adjacent first and second plate apertures of the complex aperture provide an hourglass shape extending from where the unthreaded compression ramp ends part way through the plate thickness to the bottom side of the bone plate with threaded surfaces of the immediately adjacent first and second plate apertures meeting an unthreaded intermediate portion forming the hourglass shape.

14. The assembly of claim 11 wherein the insert disc is nestable in the complex aperture of the bone plate.

15. The assembly of claim 10 wherein the insert disc is pivotable about a first longitudinal axis of the set screw received in the first, unthreaded aperture of the insert disc with the set screw threadingly engaged with the threads of the one of the first and second apertures of the bone plate to thereby provide for pivotably adjusting the position of the second aperture of the insert disc with respect to the bone plate.

16. The assembly of claim 10 wherein the insert disc is comprised of a biocompatible metal or polymer.

17. The assembly of claim 16 wherein the biocompatible material of the insert disc is relatively softer than a second material comprising the bone plate.

18. The assembly of claim 10 wherein the first and second apertures are aligned along a second longitudinal axis of the insert disc.

19. The assembly of claim 10 wherein the inlet in the insert disc is oblong.

20. The assembly of claim 10 wherein the second aperture is enclosed within the perimeter of the insert disc.

21. The assembly of claim 10 wherein both of the top and bottom surfaces of the insert disc are planar.

22. The assembly of claim 21 wherein the planar top and bottom surfaces are parallel to each other.

23. An assembly comprising an insert disc for threadingly receiving a bone screw threaded into a bone plate, the assembly comprising:
 a) a bone plate comprising:
  i) a plate thickness extending from a bone-contacting bottom side to a top side;
  ii) at least one complex aperture extending through the plate thickness from the top side to the bottom side thereof,
  iii) wherein the complex aperture comprises at least one set of immediately adjacent first and second plate apertures, and
  iv) wherein the complex aperture comprises an unthreaded compression ramp extending from an opening at the top side of the bone plate downwardly and inwardly part way through the plate thickness to a threaded lower portion providing an hourglass shape;
 b) a bone screw having threads that are adapted to threadingly engage with either one or both of the immediately adjacent first and second plate apertures of the complex aperture;
 c) an insert disc that is nestable in the complex aperture of the bone plate, the insert disc comprising:
  i) an outer sidewall providing an insert disc thickness extending from a bottom surface to a top surface of the insert disc, wherein at least one of the top and bottom surfaces is planar;
  ii) a first, unthreaded aperture extending through the insert disc thickness, wherein the first aperture comprises:
   a top region sidewall sloping downwardly and inwardly part-way through the insert disc thickness from a first diameter at the top surface to a ridge having a second diameter less than the first diameter, and a bottom region sidewall extending from the ridge to the bottom surface, wherein the bottom region sidewall is aligned substantially perpendicular to the at least one of the top and bottom planar surfaces of the insert disc;

iii) a second, threaded insert aperture extending through the insert disc thickness; and iv) an inlet that extends through the outer sidewall of the insert disc and is in open communication with the first, unthreaded aperture, but not the second, threaded aperture, v) wherein the first and second insert apertures are not in open communication with each other; and d) wherein with the insert disc contacting the bone plate, a set screw received in the first, unthreaded insert aperture is threadingly engageable with the threads of the at least one of the first and second plate apertures of the complex aperture.

\* \* \* \* \*

UNITED STATES PATENT AND TRADEMARK OFFICE
CERTIFICATE OF CORRECTION

| | | |
|---|---|---|
| PATENT NO. | : 8,784,458 B1 | Page 1 of 1 |
| APPLICATION NO. | : 12/587758 | |
| DATED | : July 22, 2014 | |
| INVENTOR(S) | : White et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 942 days.

Signed and Sealed this
Fourth Day of August, 2015

Michelle K. Lee
*Director of the United States Patent and Trademark Office*